(12) United States Patent
Ben-Hur

(10) Patent No.: US 8,883,409 B1
(45) Date of Patent: Nov. 11, 2014

(54) METHOD OF REDUCING PATHOGENS IN WHOLE BLOOD BY ILLUMINATING WITH ULTRAVIOLET LIGHT UNDER LOW OXYGEN CONDITIONS

(71) Applicant: Hemalux Technologies LLC, Loveland, CO (US)

(72) Inventor: Ehud Ben-Hur, Loveland, CO (US)

(73) Assignee: Hemalux LLC, Loveland, CO (US)

( * ) Notice: Subject to any disclaimer, the term of this patent is extended or adjusted under 35 U.S.C. 154(b) by 0 days.

(21) Appl. No.: 14/099,963

(22) Filed: Dec. 8, 2013

(51) Int. Cl.
*A61K 35/14* (2006.01)
*A01N 1/02* (2006.01)

(52) U.S. Cl.
CPC ............. *A01N 1/0294* (2013.01); *A61K 35/14* (2013.01)
USPC ............................................................ 435/2

(58) Field of Classification Search
CPC ....... A61K 35/16; A61K 35/18; A61K 35/19; A61K 35/14
See application file for complete search history.

(56) References Cited

U.S. PATENT DOCUMENTS

| 5,176,921 | A | 1/1993 | Wiesehahn |
| 5,955,256 | A | 9/1999 | Sowemimo-Coker |
| 6,970,740 | B2 | 11/2005 | Larcom |
| 8,164,073 | B2* | 4/2012 | Mohr ........................ 250/455.11 |
| 8,535,421 | B2* | 9/2013 | Yoshida et al. ...................... 96/6 |
| 2003/0078241 | A1 | 4/2003 | Hsia |
| 2006/0270017 | A1* | 11/2006 | Reiter et al. ................ 435/235.1 |
| 2013/0259744 | A1* | 10/2013 | Yoshida et al. ................. 422/44 |

FOREIGN PATENT DOCUMENTS

| WO | WO01/80939 | 11/2001 |
| WO | WO2007/076834 | 7/2007 |

OTHER PUBLICATIONS

Gupta et al., "Evaluation of random donor platelets at different temperatures for an extended shelf life", Biomedical Research (Aligarh), 21 (4) : 433-436 (2010), abstract only.*
Chin S, Williams B, Gottlieb P, et al. Virucidal short wavelength ultraviolet light treatment of plasma and factor VIII concentrate: protection of proteins by antioxidants. Blood 1995 86:4331-4336.

* cited by examiner

*Primary Examiner* — Sandra Saucier
(74) *Attorney, Agent, or Firm* — Boris Leschinsky

(57) ABSTRACT

Disclosed are methods for pathogen reduction in blood by illuminating with UV light while taking steps for preservation of blood components and reducing oxidative damage from reactive oxygen species generated during UV light exposure. Fresh whole donor blood or products derived therefrom may be submitted to UV light treatment while in a low oxygenation state defined by a partial oxygen pressure below a normal level. Such low oxygenation state occurs naturally shortly after blood collection or may be induced by exposure to low-oxygen environment, reducing temperature or by other disclosed steps.

6 Claims, No Drawings

METHOD OF REDUCING PATHOGENS IN WHOLE BLOOD BY ILLUMINATING WITH ULTRAVIOLET LIGHT UNDER LOW OXYGEN CONDITIONS

BACKGROUND

The present invention relates to methods for UV illumination of blood or a blood-derived product for the purposes of reduction of pathogens therein. More specifically, the present invention describes methods of reducing damage to blood components caused by oxygenation and generation of reactive oxygen species (ROS) during UV illumination.

A major concern in the transfusion of donated, stored whole human blood or the various blood-derived products such as blood cells or protein fractions isolated from whole blood is the presence of pathogens including viral or bacterial contamination as well as a variety of other harmful microorganisms such as parasites, molds, and yeasts. Of particular concern are the blood-borne viruses that cause hepatitis (especially hepatitis A, hepatitis B, and hepatitis C) and acquired immune deficiency syndrome (AIDS). While any number of cell washing protocols may reduce the viral contamination load for samples of blood cells by physical elution of the much smaller virus particles, such washing alone is insufficient to reduce viral contamination to safe levels. In fact, some viruses are believed to be cell-associated, and unlikely to be removed by extensive washing and centrifugal pelleting of the cells. Current theory suggests that safe levels will ultimately require at least a 5 log (5 orders of magnitude) demonstrated reduction in infectious viral titer for cellular blood components. This 5 log threshold may be even greater for plasma, protein components, especially the clotting factors (Factor VIII, Factor IX) that are administered throughout the life of some hemophilia patients.

All blood collected in the United States is now screened for a number of infectious agents including HIV-1, HIV-2, HTLV-1, hepatitis B virus, hepatitis C virus and syphilis. Additionally, donors are screened for risk factors, and potential donors are eliminated that are considered at risk for the HIV virus. This makes blood transfusion a very safe procedure. Despite these practices, there is still a risk of becoming infected by a potentially deadly virus or bacteria via the transfusion of blood or blood products. Screens for contaminants are by nature not foolproof. There is also the quite likely occurrence of new infectious agents that enter the blood supply before the significance of the event is even known.

The use of pathogen reduction technologies has the potential of eliminating the remaining risks of transmission of infectious disease as a result of blood transfusion. Various approaches have been used to sterilize blood components with the most promising being the photochemical ones, two of which were approved by regulatory agencies for pathogen reduction in platelet concentrates. The Intercept method employs a psoralen and UVA light illumination while the Mirasol method uses riboflavin and UVA+UVB light illumination.

Short wavelengths ultraviolet light (UVC, 180-290 nm) is a known sterilizing agent that targets the nucleic acids of microorganisms. It has been used for pathogen reduction in optically-transparent biological fluids such as plasma and platelet concentrates. However, in opaque biological fluids such as red cell concentrates as well as in whole blood, UVC penetration is very limited due to absorption of UVC illumination by the red cells. As a result, all attempts to use UVC illumination for sterilizing whole blood or red cells have been unsuccessful so far.

Exposure of a complex biological system such as blood to UVC results in a number of photochemical reactions that lead to degradation of blood proteins. These reactions can be divided into direct and indirect effects. Direct effects of UVC on proteins result from absorption of photons by amino acids with a relatively high absorption coefficients in the UVC range of the spectrum. These include tryptophan, phenylalanine, proline, methionine and cystein. Photon absorption results in electronic excitation of the molecule. The excited molecule can either undergo a chemical change or relax back to its ground state.

Indirect effects involve transfer of the excitation energy from a molecule to a nearby oxygen molecule resulting in formation of reactive oxygen species (ROS). ROS are strongly oxidizing agents that can react with proteins and degrade their function.

The need therefore exists for methods of donor blood preservation and pathogen inactivation in blood or blood-derived products which minimize oxidative damage to blood components caused by formation of ROS due to illuminating with UVC light.

SUMMARY

Accordingly, it is an object of the present invention to overcome these and other drawbacks of the prior art by providing novel methods of blood preservation during illumination with UVC light for the purposes of pathogen inactivation.

It is another object of the present invention to provide methods of pathogen inactivation in blood or blood-derived products by using UVC illumination while minimizing production of reactive oxygen species at the same time.

It is a further object of the present invention to provide safe methods of donor blood preservation and guarding against diminished functional status of vital blood components using exposure to UV light for the purposes of reducing pathogens such as viral and bacterial loads.

The methods of the invention include exposure of donor blood to sufficient dose of UVC light illumination to assure at least 5 log reduction of pathogen loads while at the same time reducing oxidative damage typically caused by reactive oxygen species generated as a result of such UVC illumination. This is accomplished by submitting blood or a product derived from blood to such UVC illumination while in a state of low oxygenation. The low oxygenation state may be defined by a partial oxygen pressure being below a normal level of about 160 mmHg. When donor blood is provided in such low oxygenation state, its exposure to UVC illumination does not produce toxic levels of ROS causing damage to blood components while at the same time not impeding pathogen reduction resulting from UVC light exposure.

Several methods of achieving a state of low oxygenation are described in greater detail below. They include expedited processing for UVC illumination after the initial collection from the donor using a naturally present state of low oxygenation of a fresh venous blood; reducing partial oxygen pressure by exposure of collected blood to a low-oxygen environment; as well as reducing blood temperature during UVC illumination to diminish ROS activity and subsequent damage to blood components.

DETAILED DESCRIPTION OF PREFERRED EMBODIMENTS OF THE INVENTION

The following description sets forth various examples along with specific details to provide a thorough understanding of claimed subject matter. It will be understood by those skilled in the art, however that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. The illustrative embodiments described in the detailed description and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

A typical blood collection process in developed countries includes collecting the blood from the donor's vein into a container. The amount of blood drawn varies from 200 milliliters to 550 milliliters depending on the country, but 450-500 milliliters is typical. The blood is usually stored in a flexible plastic bag that also contains sodium citrate, phosphate, dextrose, and sometimes adenine. This combination keeps the blood from clotting and preserves it during storage. This process is typically administered at a blood bank.

Following blood collection, the bag may be stored for up to 24 hours at room temperature before further processing, typically using a centrifuge to separate the whole blood into red blood cells, platelets and plasma, all of which may be then further processed and stored before use with subjects in need of blood or blood-derived products.

In addition to donor screening to avoid collecting contaminated blood, active reduction of blood-borne pathogens may be undertaken using a variety of UV-light based techniques described in the prior art based on a rationale described above.

Examples of such techniques, methods, and systems for pathogen reduction in whole blood or blood-derived products based on exposure to UVC light may be found in my co-pending U.S. patent application Ser. Nos. 13/969,543; 13/975,419; and 14/098,052—all incorporated herein by reference in their respective entireties.

One limitation of these and other known techniques of pathogen reduction using UV light is generation of reactive oxygen species during the process of UV light illumination causing subsequent damage to blood components, primarily platelets which may cause their reduced function after a transfusion to a subject other than the original blood donor.

Reactive oxygen species are chemically reactive molecules containing oxygen. Examples include super oxide anion radical, singlet oxygen and peroxides. ROS form as a natural byproduct of the normal metabolism of oxygen and have important roles in cell signaling and homeostasis. However, during times of environmental stress such as UV illumination or heat exposure, ROS levels can increase dramatically. This may result in significant damage to cell structures known as oxidative stress. In general, harmful effects of reactive oxygen species on the cell are most often seen as follows:

damage of DNA oxidations of polyunsaturated fatty acids in lipids (lipid peroxidation)

oxidations of amino acids in proteins, and oxidative inactivation of specific enzymes by oxidation of co-factors According to the present invention, the extent of production of ROS as a result of UVC illumination may be proportional to the partial oxygen pressure in the blood, or pO2. The nature of ROS also depends on the pO2 levels. At low oxygen levels, superoxide anion radical predominates while at higher oxygen levels the dominant species is singlet oxygen ($^1O_2$). The latter is much more reactive than the former and may cause significantly more oxidative damage to blood components.

The process of ROS formation as a result of blood illumination with UV light involves excitation of a ground state molecule by absorption of a UVC photon, resulting in a possibility of energy transfer to another molecule during a collision. The excited states of many organic molecules are quenched by molecular oxygen in a diffusion-controlled manner. Consequently, photochemical reactions are often drastically altered by molecular oxygen. Thus, when an excited molecule in its triplet state interacts with ground state oxygen by energy transfer, the result is a ground state molecule and an electronically excited singlet state of oxygen. $1O_2$ can react rapidly with electron-rich regions of many biomolecules such as proteins to produce oxidized species. The other type of reaction involves transfer of hydrogen or electron from the excited molecule to ground state oxygen. This results in the superoxide anion radical, which in turn can react with biomolecules or undergo dismutation. In blood exposed to UVC in the presence of oxygen, the produced ROS react primarily with amino acids of blood proteins, producing oxidative damage and loss of their function.

When blood or a product derived from blood is exposed to UVC light for pathogen reduction after storage under ambient conditions, the oxygen content of blood is equilibrated with atmospheric oxygen via diffusion to a normal partial oxygen pressure of about 160 mm Hg. Under these conditions, indirect effects of ROS formation may cause a significant amount of collateral damage to blood proteins and other blood components.

This was demonstrated by chemically removing ROS by adding ROS scavengers (e.g. rutin) during irradiation, as described in S. Chin et al *Blood* 86, 4331-4336, 1995; and G. Marx et al *Photochem. Photobiol.* 63, 541-546, 1996, all incorporated herein in their entirety by reference. Adding ROS scavengers caused a reduction in ROS which was shown to reduce protein damage to a large extent. At the same time, virus inactivation by UVC was not affected because microorganisms were killed by the direct effect of UVC on their nucleic acids. However, attempts to reduce pathogens in blood for transfusion were hampered due to a very limited window of UVC treatment, i.e. UVC light doses that left blood proteins intact resulted in only a limited pathogen reduction.

According to the present invention, at the time of collection venous fresh whole blood has a very low pO2 (may be around 15-30 mmHg), which is an order of magnitude lower than when it is allowed over time to be equilibrated with atmospheric oxygen. Therefore, if UVC treatment for pathogen reduction is applied right away or shortly after blood collection while the oxygen content is still low, indirect effects of UVC due to ROS production may be minimized. This in turn may allow using higher doses of UV illumination because the concern for ROS production may be minimized. Such higher intensity of UV light may therefore be sufficient to achieve a desired 5 log kill of pathogens. As a result, reducing pathogens with UVC shortly after donation would thus enable a more robust treatment and more effective pathogen reduction with minimal oxidative damage to blood proteins.

The methods of blood preservation and reducing pathogens of the present invention include the following steps:

a) collecting fresh whole blood from a donor;

b) providing the whole blood or a blood product derived therefrom in a low oxygenation state;

c) illuminating said blood or the blood product derived therefrom with ultraviolet light at a wavelength range from 250 nm to 280 nm with intensity sufficient to reduce pathogens therein; and d) storing the blood or the blood product derived therefrom for subsequent use with subjects other than the blood donor.

The low oxygenation state may be defined by a partial oxygen pressure of blood or a blood product derived therefrom being below a normal partial oxygen pressure of 160 mmHg. In embodiments, blood or the blood-derived product may be provided in a low oxygen state defined as a partial oxygen pressure at or below about 80 mmHg, 40 mmHg or any number between 15 mmHg and 160 mmHg. The term "about" is used here and throughout the specification to define a plus or minus deviation of 10% of the cited parameter.

Rapid initiation of UVC illumination shortly after collecting blood from the donor may provide one method of assuring blood to be in a low oxygenation state. In embodiments, the time from completing step (a) of blood collecting to initiation of step (b) of blood exposure to UVC light in the cited above wavelength range may be as low as 8 hours or less. Such rapid processing may result in a much better preservation of blood while assuring strong reduction in pathogens therein.

For logistical reasons, it may be desirable to extend the time frame for treating blood with UV illumination up to 24 hours. During that time the donor blood may be stored in blood bags with low gas permeability to avoid diffusion of oxygen into the bag.

In embodiments, the intensity of UV light illumination may be defined differently for opaque whole blood or a blood product containing red blood cells versus clear blood-derived products such as plasma, serum, etc. In the first instance, the least effective intensity of UVC light may be defined as at or above 5 Joules per $cm^2$ of blood surface, while for optically-transparent products this threshold may be defined as 0.1 Joules per $cm^2$ for plasma irradiated in a thin film or 0.3 $J/cm^2$ for platelet concentrate in a bag. The upper end of the safety limit of UVC light intensity may be defined empirically based on a specific product by evaluating the therapeutic efficacy of the blood product or component after UV-irradiation.

In addition to rapidly processing blood for UV illumination shortly after blood collection, the present invention discloses other methods of providing blood or the product derived therefrom in a state of low oxygenation. One such method may involve removing air from the blood collection bag to slow down or even eliminate entirely oxygen diffusion from such air into the venous blood.

Another method of reducing oxygen pressure in the blood prior to exposure to UV light for the purposes of pathogen reduction may involve exposure of such blood to a low-oxygen environment. In embodiments, a gas-permeable blood collection and storage bag may be exposed to a nitrogen environment, a carbon dioxide environment, an inert gas environment, or a combination thereof—for sufficient time to allow diffusion of oxygen out of the blood and through the walls of the bag into such low-oxygen environment. Such period of time may be between 8 and 24 hours depending on the bag permeability and desired degree of oxygen reduction.

Yet another method to reduce oxidative damage according to the present invention may include reducing blood temperature prior to and during exposure to UV light illumination. Reduced temperature may lead to reduced activity of ROS and limit the damage to blood components as a result. ROS are short-lived (in the range of microseconds) so reducing temperature during their generation and a short life cycle may be helpful to limit their damage and may not be extended to a period of time after UV illumination is already finished.

The degree of reducing temperature may depend on the nature of blood derived product as various blood components have different sensitivities to reduced temperature. The most sensitive blood components are platelets. For fresh blood or a blood derived product containing platelets, the temperature of such product may only be reduced from about room temperature down to 18 degrees C. at the most. At the same time, for other blood derived products which do not contain platelets, the temperature may be reduced to a much deeper level, as low as to about 1 degrees C. Deeper temperature reduction may be beneficial to further suppress harmful activity of ROS produced as a result of UV illumination.

As may be understood by those skilled in the art, any of the above mentioned methods may be combined with other methods to improve the overall results. For example, rapid processing of blood shortly after its collection may be combined with a step of reducing its temperature as described above so as to diminish oxidative damage as much as possible.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of donor blood preservation and reducing pathogens by illuminating with ultraviolet light, the method comprising the steps of:
    a) collecting fresh whole blood from a donor;
    b) providing the whole fresh blood in a low oxygenation state solely by performing step c) within 8 hours of collection, wherein a low oxygen state is defined by a partial oxygen pressure being below 160 mmHg;
    c) illuminating said whole blood with ultraviolet light at a wavelength range from 250 nm to 280 nm with intensity sufficient to reduce pathogens therein; and
    d) storing said whole blood for subsequent use with subjects other than said donor.

2. The method as in step 1, wherein said whole blood is provided in the low oxygenation state with the partial oxygen pressure thereof of 80 mmHg or less.

3. The method as in claim 2, wherein said low oxygenation state is characterized by said partial oxygen pressure at or below 40 mmHg.

4. The method as in claim 1, wherein the intensity of illumination with said ultraviolet light is above 5 Joules per $cm^2$.

5. The method as in claim 1, wherein said blood preservation is further improved by reducing temperature of said whole blood to below room temperature during said illumination by ultraviolet light in said step (c).

6. The method as in claim 5, wherein said temperature is at or above 18 degrees C.

* * * * *